United States Patent
Zhao et al.

(10) Patent No.: US 12,061,174 B1
(45) Date of Patent: Aug. 13, 2024

(54) CREEP LIFETIME PREDICTION METHOD FOR P92 MAIN STEAM PIPELINE WELDED JOINT

(71) Applicant: Tianjin University, Tianjin (CN)

(72) Inventors: Lei Zhao, Tianjin (CN); Lianyong Xu, Tianjin (CN); Kai Song, Tianjin (CN); Yongdian Han, Tianjin (CN)

(73) Assignee: Tianjin University, Tianjin (CN)

( * ) Notice: Subject to any disclaimer, the term of this patent is extended or adjusted under 35 U.S.C. 154(b) by 0 days.

(21) Appl. No.: 18/619,168

(22) Filed: Mar. 28, 2024

(30) Foreign Application Priority Data

Mar. 31, 2023 (CN) .......................... 202310330853.0

(51) Int. Cl.
  *G01N 3/02* (2006.01)
  *G01N 33/2045* (2019.01)
(52) U.S. Cl.
  CPC ........... *G01N 3/02* (2013.01); *G01N 33/2045* (2019.01); *G01N 2203/0071* (2013.01)
(58) Field of Classification Search
  CPC ................. G01N 3/02; G01N 33/2045; G01N 2203/0071
  See application file for complete search history.

(56) References Cited

U.S. PATENT DOCUMENTS

| | | | |
|---|---|---|---|
| 11,060,156 B2* | 7/2021 | Hasegawa | C22C 38/32 |
| 11,167,369 B2* | 11/2021 | Hasegawa | C21D 9/50 |
| 11,847,387 B1* | 12/2023 | Zhao | G06F 30/20 |
| 2023/0129188 A1* | 4/2023 | Hsu | H04L 67/10 |
| | | | 706/12 |

FOREIGN PATENT DOCUMENTS

| | | |
|---|---|---|
| CN | 105675334 | 6/2016 |
| CN | 113533674 | 10/2021 |
| CN | 115496707 | 12/2022 |

OTHER PUBLICATIONS

Fujio Abe, "Creep rupture ductility of Gr.91 and Gr.92 at 550° C to 700° C", Materials at High Temperatures, vol. 37, No. 4, May 29, 2020, pp. 243-255.

Kazuhiro Kimura et al., "Evaluation of Long-Term Creep Strength of ASME Grades 91, 92, AND 122 Type Steels", Proceedings of the ASME 2012 Pressure Vessels and Piping Conference, vol. 6: Materials and Fabrication, Jul. 15-19, 2012, pp. 309-316.

* cited by examiner

*Primary Examiner* — Jonathan M Dunlap
(74) *Attorney, Agent, or Firm* — JCIPRNET

(57) ABSTRACT

The disclosure discloses a creep lifetime prediction method for a P92 main steam pipeline welded joint, which includes the following. Based on the minimally invasive sampling technology and the microstructure characterization equipment, the microstructure of the P92 steel welded joint after service is obtained. An area with a most significant degradation of the P92 steel welded joint is determined by performing grading processing on the microstructure of the welded joint. The maximum main stress of the structural component is obtained through the finite element technology and the actual service pressure of the P92 steel welded component. Through the maximum main stress and the microstructure after grading, based on the temperature-related Larson-Miller creep lifetime prediction method, the creep lifetime of the welded joint under the condition is determined.

8 Claims, 4 Drawing Sheets

(a)

CREEP LIFETIME PREDICTION METHOD FOR P92 MAIN STEAM PIPELINE WELDED JOINT

CROSS-REFERENCE TO RELATED APPLICATION

This application claims the priority benefit of China application serial no. 202310330853.0, filed on Mar. 31, 2023. The entirety of the above-mentioned patent application is hereby incorporated by reference herein and made a part of this specification.

BACKGROUND

Technical Field

The disclosure relates to the technical field of creep lifetime prediction of a P92 steel welded joint of martensitic heat-resistant steel commonly used in the power industry, and particularly relates to a creep lifetime prediction method for a P92 main steam pipeline welded joint.

Description of Related Art

P92 steel is a 9Cr martensitic heat-resistant steel used in ultra (super) critical units of 550° ° C. to 630° C. Since the steel has good creep strength, and oxidation resistance and is also economical, the P92 steel has been widely used in key components such as the main steam pipeline, the reheater, and the box body of the ultra (super) critical units. Since the P92 steel components often serve under high temperature conditions, during the long-term process of creep load, precipitate phase coarsening, creep voids, and micro-cracks could occur, and the creep strength of the material is reduced. At the same time, the structural components are inevitably connected using the welding process. However, the microstructure and properties of the weld area and the heat-affected area in the welded joint are often quite different from the base metal, which in turn causes creep rupture failure of the structural components to occur at the welded joint. In particular, taking the 9Cr martensitic steel as an example, type IV cracks often appear in the heat-affected area of the welded joint, which significantly reduces the creep strength of the material and ultimately leads to fracture. In addition, in the existing creep lifetime prediction methods, such as Larson-Miller extrapolation method, Monkman-Grant extrapolation method, θ projection method, and finite element damage calculation method, generally, long-term creep data are used to perform extrapolation prediction for the creep lifetime of the base material under actual working conditions. For the welded joint, in the American ASME NH standard and the France RCC MRx standard, the reduction coefficient is recommended to use as a bridge between the creep strengths of the P92 steel welded joint and the base material. However, when the microhardness of the P92 structural component is lower than a certain value, the remaining creep lifetime of the component decreases rapidly, which means that when the P92 steel material degrades to a certain point, the creep strength of the material changes significantly. In the conventional creep lifetime prediction methods, the rapid decrease in the creep strength caused by material degradation is ignored. Therefore, considering the evolution of the microstructure and creep voids in the creep process and developing a creep lifetime prediction method for the P92 main steam pipeline welded joint based on a technology of grading the microstructure is of great significance for accurately assessing the remaining service life of the P92 steel structural components under high temperature creep conditions.

SUMMARY

In order to solve the above problems, the purpose of this disclosure is to propose a creep lifetime prediction method for a P92 main steam pipeline welded joint based on a technology of grading a microstructure to meet the development needs of accurate creep lifetime prediction under material degradation conditions, this method can effectively solve the problems of existing prediction methods such as incomplete consideration of the microstructure during the creep process, and a new method for the creep performance assessment of the P92 steel welded components serving under complex working conditions is provided.

In order to achieve the above technical purpose, the disclosure provides a creep lifetime prediction method for a P92 main steam pipeline welded joint, which includes the following.

A microstructure of a P92 steel welded joint under service is collected, and an area with a most significant degradation of the P92 steel welded joint is determined by performing grading processing on the microstructure.

A maximum main stress of the P92 steel welded joint is obtained based on an actual service pressure of the P92 steel welded joint and according to a finite element technology.

Considering a service environment temperature, the microstructure after grading, and the maximum main stress, a creep lifetime prediction model is established to predict a creep lifetime of the P92 steel welded joint under service conditions, in which the creep lifetime prediction model is expressed as:

$$P_{LM}=(T+273.15)[C+lg(t_r)]=a_0+a_1 \cdot lg(\sigma)+a_2 \cdot [lg(\sigma)]^2$$

In the formula, $P_{LM}$ is a Larson-Miller coefficient; T is the service environment temperature; C, $a_0$, $a_1$, and $a_2$ are material constants; $t_r$ is a creep rupture time; and σ is the maximum main stress.

Preferably, in a process of collecting the microstructure of the P92 steel welded joint after service, the microstructure is obtained by sampling the heat-affected area, a weld area, and a base material area of the P92 steel welded joint.

Preferably, in a process of determining the area with the most significant degradation, a quantity of creep voids, a size of the creep void, and a size of a Laves phase of the microstructure are obtained, and grading processing is performed on the microstructure through a dichotomy method to determine the area with the most significant degradation of the P92 steel welded joint.

Preferably, in a process of performing grading processing on the microstructure, grading standards of the microstructure are as follows.

Level I: The creep voids begin to appear in the critical area or the fine-grained area in the heat-affected area of the P92 steel welded joint. The creep voids only appear individually at grain boundaries of individual grain. The quantity of creep voids on each grain is not greater than 1; the average size of the creep voids is 4 to 5 μm; and the average length of the Laves phase is less than 0.85 μm.

Level II: The creep voids appear at multiple grain boundaries of a grain in the critical area and the fine-grained area in the heat-affected area of the P92 steel welded joint. The quantity of creep voids on each grain boundary of each grain is not greater than 1; the average size of the creep voids is 5 to 7.5 μm; and the average length of the Laves phase is 0.85 to 1 μm.

Level III: The creep voids appear at multiple grain boundaries of a grain in the critical area and the fine-grained area in the heat-affected area of the P92 steel welded joint. The quantity of creep voids on each grain boundary of each grain is greater than or equal to 2, and the creep voids do not aggregate; the distance between adjacent creep voids is greater than the diameter of the creep voids; the average size of the creep voids is 7.5 to 10 μm; and the average length of the Laves phase is 1 to 1.15 μm.

Level IV: The creep voids aggregate at grain boundaries of multiple grains in the critical area and the fine-grained area in the heat-affected area of the P92 steel welded joint or micro-cracks appear at the grain boundaries. The average size of the creep voids is 10 to 15 μm; and the average length of the Laves phase is 1.15 to 1.3 μm.

Preferably, in a process of obtaining the maximum main stress of the P92 steel welded joint, a size of the main steam pipeline having the P92 steel welded joint, the actual service pressure, and a stress state are the input data for calculation in ABAQUS software. Then, the maximum main stress is obtained.

Preferably, in a process of obtaining the creep lifetime, based on the grading standards of the microstructure, lifetime prediction is performed through the creep lifetime prediction model, and the creep lifetime generated according to the grading standard is obtained.

Preferably, in a process of generating the creep lifetime according to the grading standards, a lifetime of the P92 steel welded joint of the microstructure under the level I is 60% of a lifetime predicted of the creep lifetime prediction model.

The lifetime of the P92 steel welded joint of the microstructure under the level II is 45% of the lifetime predicted of the creep lifetime prediction model.

The lifetime of the P92 steel welded joint of the microstructure under the level III is 20% of the lifetime predicted of the creep lifetime prediction model.

The lifetime of the P92 welded joint of the microstructure under the level IV is 5% of the lifetime predicted of the creep lifetime prediction model.

Preferably, a creep lifetime prediction system used to implement the creep lifetime prediction method includes the following.

A degradation identification module is used to determine the area with the most significant degradation of the P92 steel welded joint by collecting the microstructure of the P92 steel welded joint after service and performing grading processing on the microstructure.

A main stress calculation module is used to obtain the maximum main stress of the P92 steel welded joint according to an identification result of the degradation identification module, based on the actual service pressure of the P92 steel welded joint, and based on the finite element technology.

A creep lifetime prediction module is used to establish the creep lifetime prediction model to predict the creep lifetime of the P92 steel welded joint under the service conditions under the premise of considering the service environment temperature and according to the microstructure after grading and the maximum main stress, in which the creep lifetime prediction model is expressed as:

$$P_{LM}=(T+273.15)[C+lg(t_r)]=a_0+a_1 \cdot lg(\sigma)+a_2 \cdot [lg(\sigma)]^2$$

In the formula, $P_{LM}$ is the Larson-Miller coefficient; T is the service environment temperature; C, $a_0$, $a_1$, and $a_2$ are the material constants; $t_r$ is the creep rupture time; and σ is the maximum main stress.

Preferably, the degradation identification module is further configured to perform grading on a microstructure of a P92 steel welded joint in service according to the grading standards and determine the area with the most significant degradation based on a grading result.

Preferably, the creep lifetime prediction module is further configured to predict a lifetime of the P92 steel welded joint in service through the creep lifetime prediction model, and obtain the creep lifetime based on different grading results according to the grading results.

The disclosure discloses technical effects as follows.

The disclosure considers the reduction of creep lifetime caused by the degradation of the microstructure in the creep process and incorporates the reduction into the lifetime assessment of the P92 steel welded joint, which makes up for the shortcomings of conventional lifetime prediction methods in the aspect of the evolution of the microstructure. Areas of positions prone to failure of the P92 steel welded joint component are calculated by using the finite element method, which solves the limitation that the conventional creep lifetime prediction methods cannot be directly applied to engineering components. The accuracy of the remaining lifetime prediction is improved, safe and stable operation of components serving under high temperature creep conditions are ensured, and the economic losses caused by pipeline maintenance and replacement are reduced.

BRIEF DESCRIPTION OF THE DRAWINGS

In order to describe the embodiments of the disclosure or the technical solutions in the related art more clearly, the following will briefly introduce the drawings to be used to illustrate the embodiments in the disclosure. Certainly, the drawings in the following description are only some embodiments of the disclosure. For persons of ordinary skill in the art, without exerting any creative effort, the persons may also acquire additional drawings based on the drawings.

DESCRIPTION OF THE EMBODIMENTS

Figure 1:
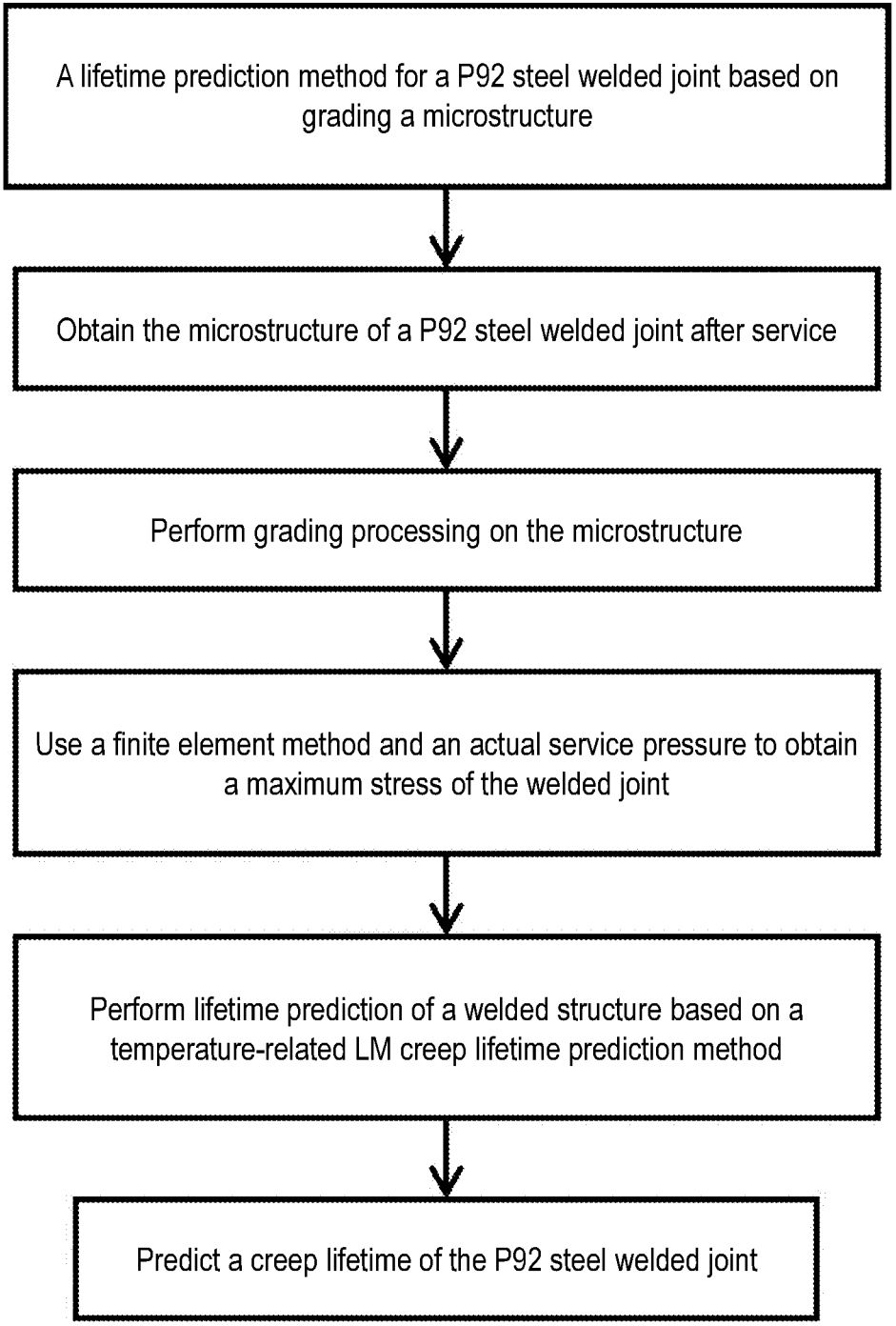
FIG. 1 is a schematic diagram of a research route of a creep lifetime prediction method for a P92 main steam pipeline welded joint based on a technology of grading a microstructure according to an embodiment of the disclosure.

In order to make the purpose, technical solutions, and advantages of the embodiments of the disclosure clearer, the following will be implemented together with the accompanying drawings of the embodiments, and clearly and completely describe the technical solutions in the embodiments of the disclosure. Certainly, the embodiments described are only a part of the embodiments of the disclosure, not all embodiments. Generally, components of the embodiments described and illustrated in the drawings herein may be arranged and designed in a variety of different configurations. Accordingly, the following detailed description of the embodiments of the disclosure provided in the drawings is not intended to limit the scope of protection of the appended claims, but rather to merely represent selected embodiments of the disclosure. Based on the embodiments of the disclosure, all other embodiments obtained by persons skilled in the art without any creative work fall within the scope of protection of the disclosure.

As shown in FIGS. 1 to 6, the disclosure provides a creep lifetime prediction method for a P92 main steam pipeline welded joint based on a technology of grading a microstructure, which includes the following.

Step 1: Based on the portable minimally invasive sampling machine (Application No.: 201610118068.9), a heat-affected area, a weld area, and a base material area of a P92 steel main steam pipeline welded joint in service are sampled respectively to prepare observation samples of the microstructure and microhardness testing samples.

Step 2: Based on the observation samples in step 1, structural features of the heat-affected area, the weld area, and the base material area of a P92 steel main steam pipeline welded joint after service are identified, and the structural features mainly include the quantity and size of creep voids and the size of the Laves phase.

Step 3: Based on the structural features of the P92 steel main steam pipeline after service in step 2, statistics are calculated on the size and quantity of the creep voids and the size of the Laves phase in twenty fields of view by using the dichotomy method, and grading is performed on the P92 steel main steam pipeline welded joint.

Specifically, grading standards of the microstructure are as follows.

Level I: The creep voids begin to appear in the critical area or the fine-grained area in the heat-affected area of the P92 steel welded joint. The creep voids only appear individually at grain boundaries of individual grain. The quantity of creep voids on each grain is not greater than 1; the average size of the creep voids is 4 to 5 μm; and the average length of the Laves phase is less than 0.85 μm.

Level II: The creep voids appear at multiple grain boundaries of a grain in the critical area and the fine-grained area in the heat-affected area of the P92 steel welded joint. The quantity of creep voids on each grain boundary of each grain is not greater than 1; the average size of the creep voids is 5 to 7.5 μm; and the average length of the Laves phase is 0.85 to 1 μm.

Level III: The creep voids appear at multiple grain boundaries of a grain in the critical area and the fine-grained area in the heat-affected area of the P92 steel welded joint. The quantity of creep voids on each grain boundary of each grain is greater than or equal to 2, and the creep voids do not aggregate; the distance between adjacent creep voids is greater than the diameter of the creep voids; the average size of the creep voids is 7.5 to 10 μm; and the average length of the Laves phase is 1 to 1.15 μm.

Level IV: The creep voids aggregate at grain boundaries of multiple grains in the critical area and the fine-grained area in the heat-affected area of the P92 steel welded joint or micro-cracks appear at the grain boundaries. The average size of the creep voids is 10 to 15 μm; and the average length of the Laves phase is 1.15 to 1.3 μm.

Step 4: Based on the size of the P92 steel main steam pipeline, the service pressure, and the stress state, a maximum main stress level of the P92 main steam pipeline welded joint of the minimally invasive sampling is calculated by using ABAQUS software, and the creep lifetime of the P92 steel base material at the stress level is determined by using the temperature-related Larson-Miller relation of the stress of the welded joint-creep rupture lifetime.

Step 5: Based on the structural state observed in step 2, the grading standards of the microstructure in step 3, and the creep lifetime of the P92 steel base material at the maximum main stress level in step 4, the remaining creep lifetime of the P92 steel welded joint is calculated.

Specifically, the lifetime of the P92 steel welded joint of the microstructure under level I is 60% of the lifetime calculated in step 4; the lifetime of the P92 steel welded joint of the microstructure under level II is 45% of the lifetime calculated in step 4; the lifetime of the P92 steel welded joint of the microstructure under level III is 20% of the lifetime calculated in step 4; and the lifetime of the welded joint of the microstructure under level IV is 5% of the lifetime calculated in step 4.

Embodiment 1. Please refer to FIG. 1. The creep lifetime prediction method for the P92 main steam pipeline welded joint based on the technology of grading the microstructure includes the following. Based on the minimally invasive sampling technology and the microstructure characterization equipment, the microstructure of the P92 steel welded joint after service is obtained. An area with a most significant degradation of the P92 steel welded joint is determined by performing grading processing on the microstructure of the welded joint. The maximum main stress of the structural component is obtained through the finite element technology and the actual service pressure of the P92 steel welded component. Through the maximum main stress and the microstructure after grading, based on the temperature-related Larson-Miller creep lifetime prediction method, the creep lifetime of the welded joint under the condition is determined. Details of the disclosure are further described, and the test material is a P92 martensitic heat-resistant steel welded joint.

Figure 2:
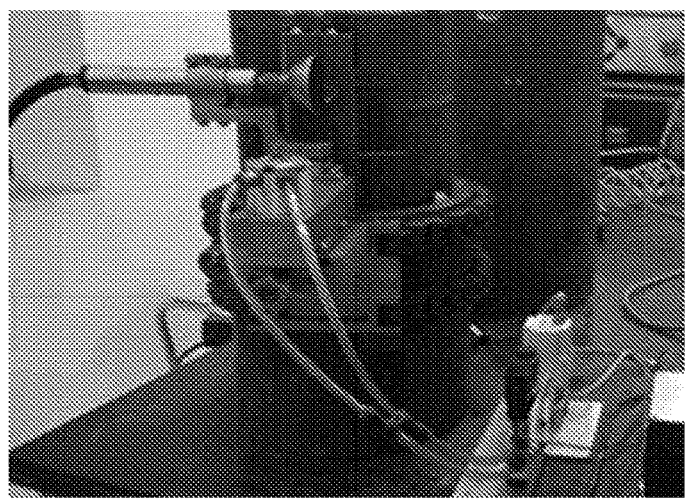
FIG. 2 is a schematic diagram of sampling by a portable sampling machine according to an embodiment of the disclosure.

Step 1: Based on the portable minimally invasive sampling machine (Application No.: 201610118068.9), a heat-affected area, a weld area, and a base material area of the P92 steel main steam pipeline welded joint in service are sampled respectively to prepare observation samples of the microstructure and microhardness testing samples, as shown in FIG. 2.

Figure 3:
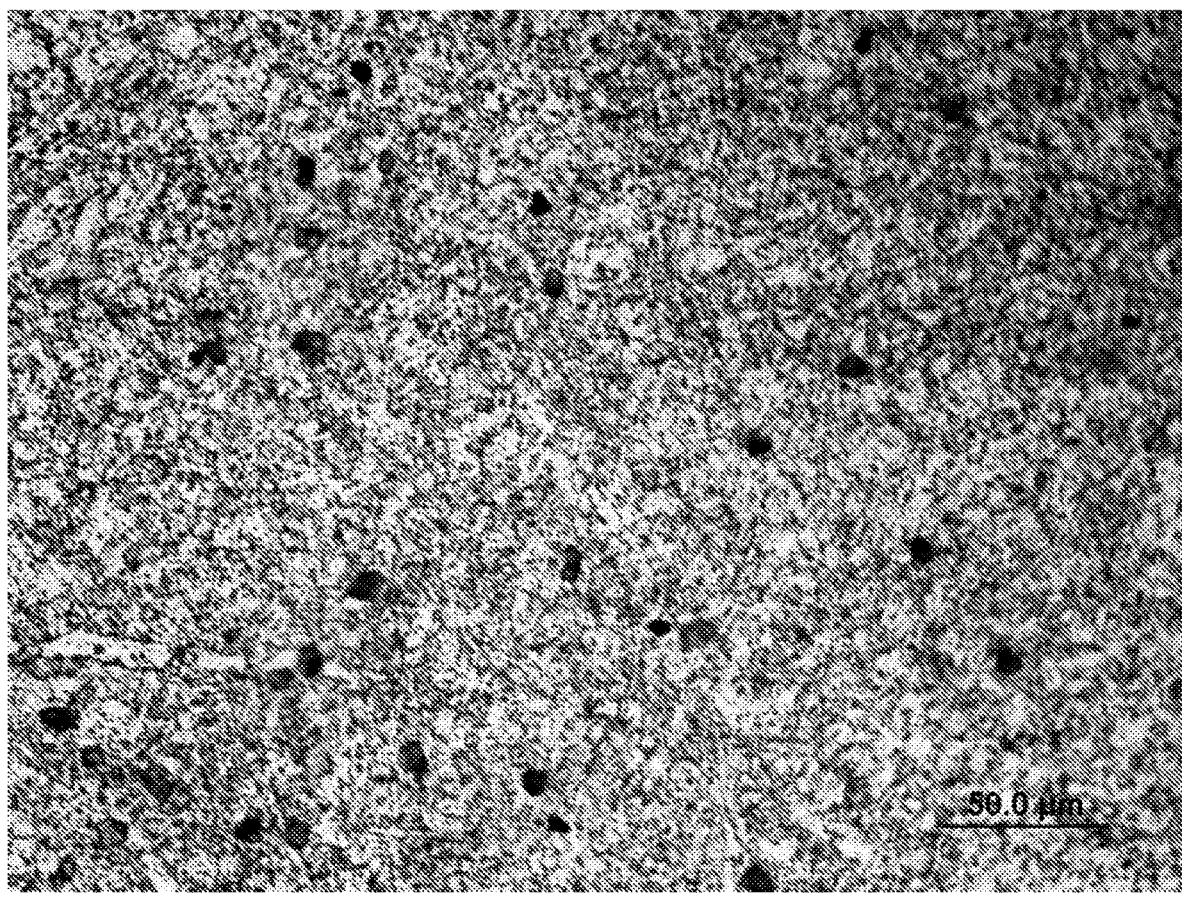
FIG. 3 shows creep voids in a fine-grained area of the P92 steel welded joint under a creep condition of 4000 h according to an embodiment of the disclosure.
Figure 4:
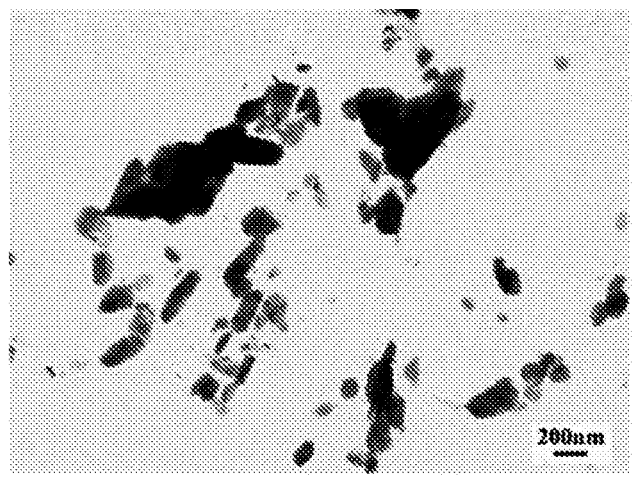
FIG. 4 is a Laves phase of the fine-grained area of the P92 steel welded joint under a creep condition of 4000 h according to an embodiment of the disclosure.

Step 2: Based on the observation samples in step 1, structural features of the heat-affected area, the weld area, and the base material area of the P92 steel main steam pipeline welded joint after service are identified, and the structural features mainly include the quantity and size of creep voids and the size of the Laves phase, as shown in FIGS. 3 and 4. It may be found from FIGS. 3 and 4 that when the creep time is 4000 h, significant creep voids appear inside the material, and the Laves phase appears coarse and irregular in shape.

Step 3: Based on the structural features of the P92 steel main steam pipeline after service in step 2, statistics are calculated on the size and quantity of the creep voids and the size of the Laves phase in twenty fields of view by using the dichotomy method, and grading is performed on the P92 steel main steam pipeline welded joint. In FIG. 3, the creep voids in the fine-grained area of the P92 steel are distributed on multiple grain boundaries of a grain, and the average size is 5 μm. In FIG. 4, the average size of the Laves phase in the fine-grained area of the P92 steel is 0.5 μm. By comparing the grading standards of the microstructure proposed, it may be concluded that when the creep time is 4000 h, the grading level of the P92 steel welded joint is level I.

Figure 5:
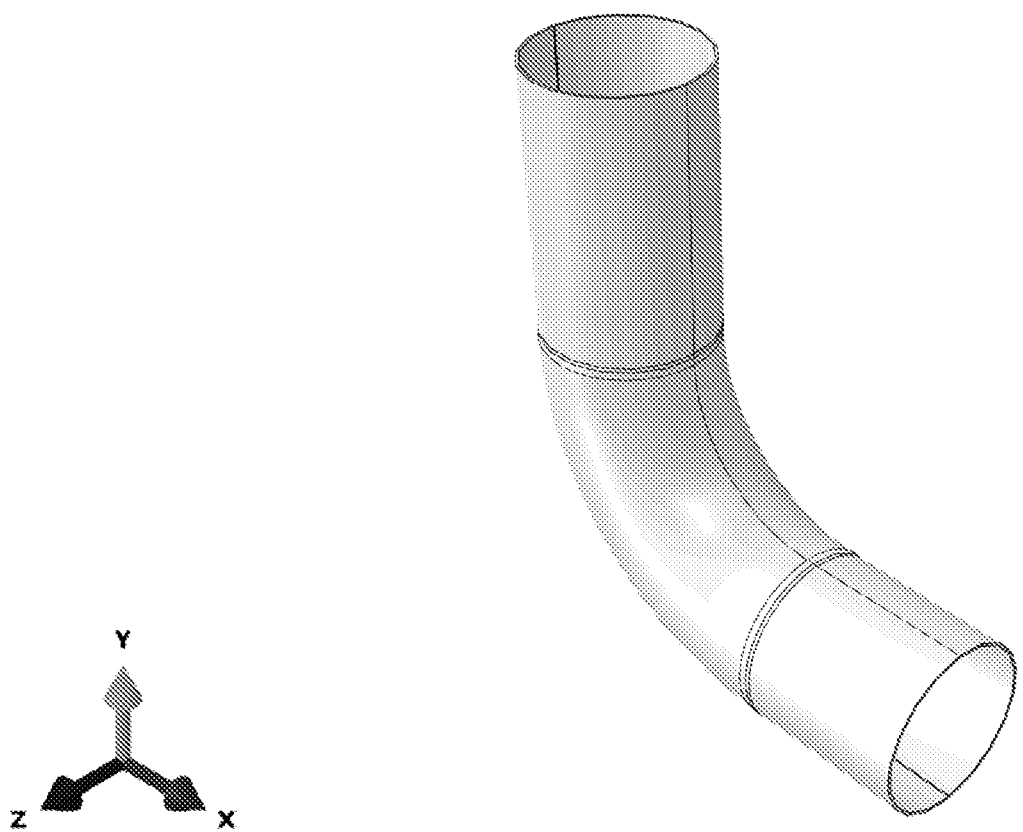
FIG. 5 is a schematic diagram of a finite element model of the P92 steel welded joint component according to an embodiment of the disclosure.
Figure 6:
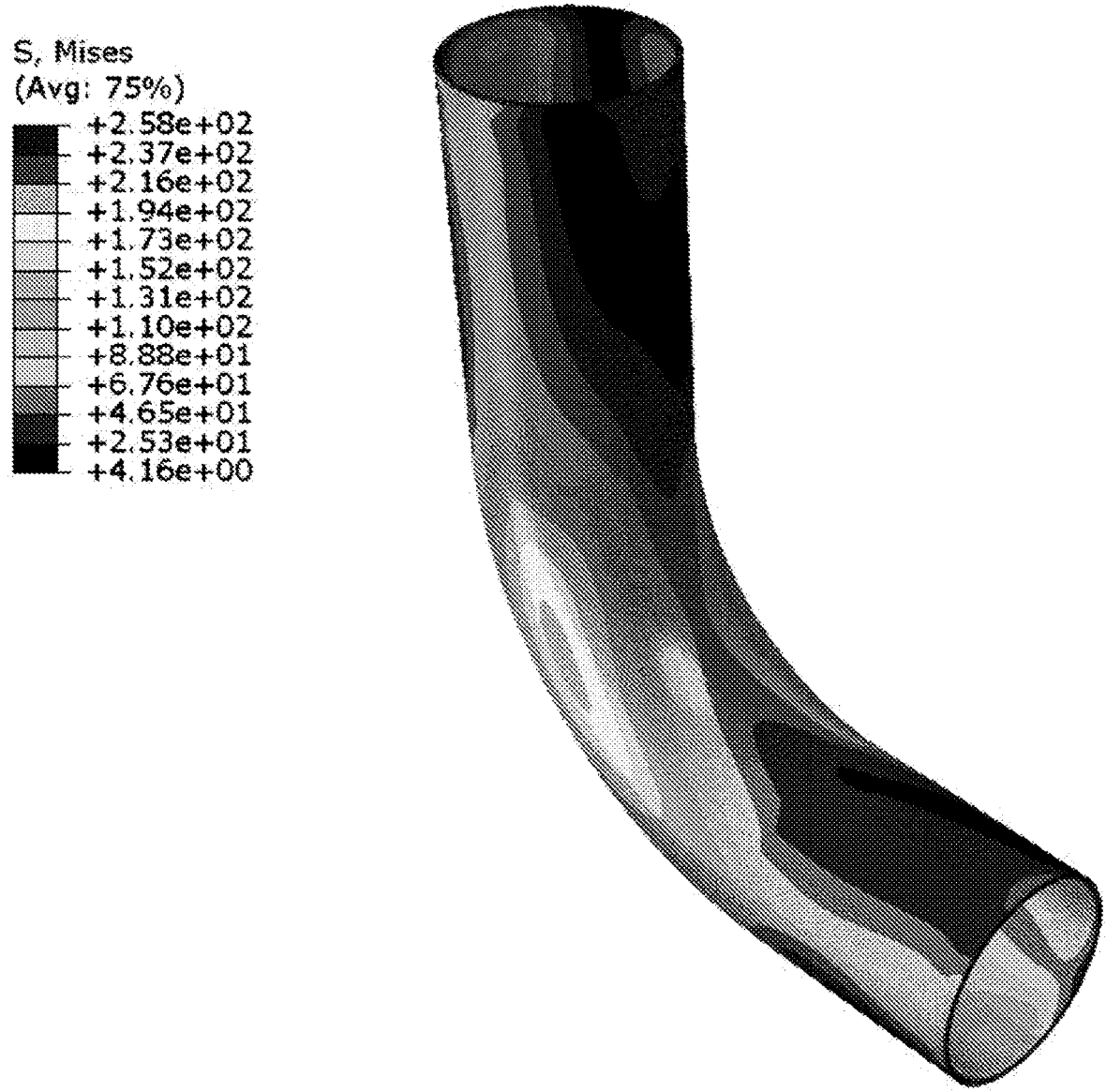
FIG. 6 is a schematic diagram of a finite element calculation result of the P92 steel welded joint component according to an embodiment of the disclosure.

Step 4: Based on the size of the P92 steel main steam pipeline, the service pressure, and the stress state, a maximum main stress level of the P92 main steam pipeline welded joint of the minimally invasive sampling is calculated by using ABAQUS software, and the creep lifetime of the P92 steel base material at the stress level is determined by using the temperature-related Larson-Miller relation of the stress of the welded joint-creep rupture lifetime. According to the parameters of the pipeline provided, a finite element model based on the ABAQUS software is established, as shown in FIG. 5. The parameters used in the model are as follows: the outer diameter is 813 mm, the wall thickness is 15 mm, the radius of the bend pipeline is 1219 mm, the length of the upper straight pipeline section is 1450 mm, and the length of the right straight pipeline section is 950 mm. According to the weld process and metallographic observation, girth weld areas are drawn at two ends of the straight pipeline section, and a heat-affected area of a certain width is set according to the actual weld condition. When performing the finite element calculation, a fixed constraint is imposed on the end surface of the right straight pipeline section, and force, torque, and internal pressure are applied on the end surface of the upper straight pipeline section according to the actual situation. The load parameters used in the model are as follows: the values of the force (X direction: −28083 N, Y direction: −4863 N, Z direction: −10281 N), the values of the torque (X direction: −88055 N·M, Y direction: 102593 N·M, Z direction: 217625 N·M), and the internal pressure is 1.5 MPa. The stress distribution cloud diagram of the P92 steel welded joint component after applying the load is shown in FIG. 6. It may be found from the drawing that the maximum main stress level under the condition is 258 MPa. According to the creep strength of the P92 steel at a condition of 550° C. provided by Fujio Abe (Abe F. Creep rupture ductility of Gr. 91 and Gr. 92 at 550° ° C. to 700° C. [J]. Materials at High Temperatures, 2020, 37(4): 243-255.), and by using the Larson-Miller equation, as shown in the following formula, the fitting of the creep lifetime prediction formula is performed.

$$P_{LM}=(T+273.15)[C+lg(t_r)]=a_0+a_1 \cdot lg(\sigma)+a_2 \cdot [lg(\sigma)]^2$$

In the formula, $P_{LM}$ is a Larson-Miller coefficient; T is a service environment temperature; C, $a_0$, $a_1$, and $a_2$ are material constants; $t_r$ is a creep rupture time; and σ is the maximum main stress.

Kimura and Takahashi give the Larson-Miller material parameters of the P92 steel base material under the creep condition (Kimura, K, & Takahashi, Y. "Evaluation of Long-Term Creep Strength of ASME Grades 91, 92, and 122 Type Steels." Proceedings of the ASME 2012 Pressure Vessels and Piping Conference. Volume 6: Materials and Fabrication, Parts A and B. Toronto, Ontario, Canada. Jul. 15-19, 2012. pp. 309-316. ASME.) In the literature, C=24.9556, $a_0$=28473.7, $a_1$=3409.2, and $a_2$=−2191.8. Through calculation, the creep lifetime of the P92 steel base material at 258 MPa is 23948.1 h.

Step 5: Based on the structural state observed in step 2, the grading standards of the microstructure in step 3, and the creep lifetime of the P92 steel base material at the maximum main stress level in step 4, the remaining creep lifetime of the P92 steel welded joint is calculated. When the creep time is 4000 h, the lifetime of the P92 steel welded joint of the microstructure under level I is 60% of the lifetime calculated in step 4, that is, the remaining creep lifetime is 14368.9 h.

In the description throughout the document, the description of reference terms such as "an embodiment," "embodiments," "examples," "specific examples," or "some examples" means that the specific features, structures, materials, or characteristics described in connection with the embodiment or example are included in at least one embodiment or example according to the disclosure. Throughout the document, schematic expressions of the above terms do not necessarily refer to the same embodiment or example. Furthermore, the specific features, structures, materials, or characteristics described may be combined in any suitable manner in any one or more embodiments or examples. In addition, persons skilled in the art may combine and arrange different embodiments or examples and features of different embodiments or examples described in the document as long as no conflict is present.

Although preferred embodiments of the disclosure have been described, persons skilled in the art, once informed of the basic inventive concepts, may make additional changes and modifications to the embodiments. Therefore, it is intended that the appended claims be construed to include the preferred embodiments and all changes and modifications that fall within the scope of the disclosure.

What is claimed is:

1. A creep lifetime prediction method for a P92 main steam pipeline welded joint, comprising:
   collecting a microstructure of a P92 steel welded joint after service, and determining an area with a most significant degradation of the P92 steel welded joint by performing grading processing on the microstructure, wherein in a process of determining the area with the most significant degradation, a quantity of creep voids, a size of the creep void, and a size of a Laves phase of the microstructure are obtained, and grading processing is performed on the microstructure through a dichotomy method to determine the area with the most significant degradation of the P92 steel welded joint;
   grading standards of the microstructure are:
   a level I: the creep voids begin to appear in a critical area or a fine-grained area in a heat-affected area of the P92 steel welded joint, and the creep voids only appear individually at grain boundaries of individual grain, wherein a quantity of the creep voids on each of the grain is not greater than 1, an average size of the creep voids is 4 to 5 μm, and an average length of the Laves phase is less than 0.85 μm;
   a level II: the creep voids appear at a plurality of grain boundaries of a grain in the critical area and the fine-grained area in the heat-affected area of the P92 steel welded joint, wherein a quantity of the creep voids on each of the grain boundaries of each of the grain is not greater than 1, the average size of the creep voids is 5 to 7.5 μm, and the average length of the Laves phase is 0.85 to 1 μm;
   a level III: the creep voids appear at the plurality of grain boundaries of the grain in the critical area and the fine-grained area in the heat-affected area of the P92 steel welded joint, the quantity of the creep voids on each of the grain boundaries of each of the grain is greater than or equal to 2 and the creep voids do not aggregate, and a distance between adjacent creep voids is greater than a diameter of the creep void, wherein the average size of the creep voids is 7.5 to 10 μm, and the average length of the Laves phase is 1 to 1.15 μm;

a level IV: the creep voids aggregate at the grain boundaries of the plurality of grains in the critical area and the fine-grained area in the heat-affected area of the P92 steel welded joint or micro-cracks appear at the grain boundaries, wherein the average size of the creep voids is 10 to 15 μm, and the average length of the Laves phase is 1.15 to 1.3 μm;

obtaining a maximum main stress of the P92 steel welded joint based on an actual service pressure of the P92 steel welded joint and according to a finite element technology;

establishing a creep lifetime prediction model to predict a creep lifetime of the P92 steel welded joint under service conditions under a premise of considering a service environment temperature and according to the microstructure after grading and the maximum main stress, wherein the creep lifetime prediction model is expressed as:

$$P_{LM}=(T+273.15)[C+lg(t_r)]=a_0+a_1\cdot lg(\sigma)+a_2\cdot [lg(\sigma)]^2;$$

in the formula, $P_{LM}$ is a Larson-Miller coefficient; T is the service environment temperature; C, $a_0$, $a_1$, and $a_2$ are material constants; $t_r$ is a creep rupture time; and σ is the maximum main stress;

in a process of obtaining the creep lifetime, based on the grading standards of the microstructure, lifetime prediction is performed through the creep lifetime prediction model, and the creep lifetime generated according to the grading standard is obtained;

in a process of generating the creep lifetime according to the grading standards, a lifetime of the P92 steel welded joint of the microstructure under the level I is 60% of a lifetime predicted of the creep lifetime prediction model;

the lifetime of the P92 steel welded joint of the microstructure under the level II is 45% of the lifetime predicted of the creep lifetime prediction model;

the lifetime of the P92 steel welded joint of the microstructure under the level III is 20% of the lifetime predicted of the creep lifetime prediction model; and the lifetime of the P92 welded joint of the microstructure under the level IV is 5% of the lifetime predicted of the creep lifetime prediction model.

2. The creep lifetime prediction method for the P92 main steam pipeline welded joint according to claim 1, wherein in a process of collecting the microstructure of the P92 steel welded joint after service comprises:

obtaining the microstructure by sampling the heat-affected area, a weld area, and a base material area of the P92 steel welded joint.

3. The creep lifetime prediction method for the P92 main steam pipeline welded joint according to claim 2, wherein in a process of obtaining the maximum main stress of the P92 steel welded joint comprises:

obtaining a size of the main steam pipeline having the P92 steel welded joint, the actual service pressure, and a stress state; and calculating to generate the maximum main stress according to an ABAQUS software.

4. A creep lifetime prediction system for a P92 main steam pipeline welded joint, using the creep lifetime prediction method according to claim 3, comprising:

a degradation identification module, configured to determine an area with a most significant degradation of the P92 steel welded joint by collecting the microstructure of the P92 steel welded joint after service and performing grading processing on the microstructure;

a main stress calculation module, configured to obtain the maximum main stress of the P92 steel welded joint according to an identification result of the degradation identification module, based on the actual service pressure of the P92 steel welded joint, and based on the finite element technology;

a creep lifetime prediction module, configured to establish the creep lifetime prediction model to predict the creep lifetime of the P92 steel welded joint under the service conditions under the premise of considering the service environment temperature and according to the microstructure after grading and the maximum main stress, wherein the creep lifetime prediction model is expressed as:

$$P_{LM}=(T+273.15)[C+lg(t_r)]=a_0+a_1\cdot lg(\sigma)+a_2\cdot [lg(\sigma)]^2;$$

in the formula, $P_{LM}$ is the Larson-Miller coefficient; T is the service environment temperature; C, a0, a1, and a2 are the material constants; $t_r$ is the creep rupture time; and σ is the maximum main stress.

5. A creep lifetime prediction system for a P92 main steam pipeline welded joint, using the creep lifetime prediction method according to claim 2, comprising:

a degradation identification module, configured to determine an area with a most significant degradation of the P92 steel welded joint by collecting the microstructure of the P92 steel welded joint after service and performing grading processing on the microstructure;

a main stress calculation module, configured to obtain the maximum main stress of the P92 steel welded joint according to an identification result of the degradation identification module, based on the actual service pressure of the P92 steel welded joint, and based on the finite element technology;

a creep lifetime prediction module, configured to establish the creep lifetime prediction model to predict the creep lifetime of the P92 steel welded joint under the service conditions under the premise of considering the service environment temperature and according to the microstructure after grading and the maximum main stress, wherein the creep lifetime prediction model is expressed as:

$$P_{LM}=(T+273.15)[C+lg(t_r)]=a_0+a_1\cdot lg(\sigma)+a_2\cdot [lg(\sigma)]^2;$$

in the formula, PLM is the Larson-Miller coefficient; T is the service environment temperature; C, a0, a1, and a2 are the material constants; $t_r$ is the creep rupture time; and σ is the maximum main stress.

6. A creep lifetime prediction system for a P92 main steam pipeline welded joint, using the creep lifetime prediction method according to claim 1, comprising:

a degradation identification module, configured to determine an area with a most significant degradation of the P92 steel welded joint by collecting the microstructure of the P92 steel welded joint after service and performing grading processing on the microstructure;

a main stress calculation module, configured to obtain the maximum main stress of the P92 steel welded joint according to an identification result of the degradation identification module, based on the actual service pressure of the P92 steel welded joint, and based on the finite element technology;

a creep lifetime prediction module, configured to establish the creep lifetime prediction model to predict the creep lifetime of the P92 steel welded joint under the service conditions under the premise of considering the service environment temperature and according to the microstructure after grading and the maximum main stress, wherein the creep lifetime prediction model is expressed as:

$$P_{LM}=(T+273.15)[C+lg(t_r)]=a_0+a_1 \cdot lg(\sigma)+a_2 \cdot [lg(\sigma)]^2;$$

in the formula, $P_{LM}$ is the Larson-Miller coefficient; T is the service environment temperature; C, $a_0$, $a_1$, and $a_2$ are the material constants; $t_r$ is the creep rupture time; and $\sigma$ is the maximum main stress.

7. The creep lifetime prediction system for the P92 main steam pipeline welded joint according to claim 6, wherein the degradation identification module is further configured to perform grading on a microstructure of a P92 steel welded joint in service according to the grading standards and determine the area with the most significant degradation based on a grading result.

8. The creep lifetime prediction system for the P92 main steam pipeline welded joint according to claim 7, wherein the creep lifetime prediction module is further configured to predict a lifetime of the P92 steel welded joint in service through the creep lifetime prediction model, and obtain the creep lifetime based on different grading results according to the grading results.

\* \* \* \* \*